United States Patent
Ravikumar

(10) Patent No.: US 7,276,037 B2
(45) Date of Patent: Oct. 2, 2007

(54) COMPRESSION APPARATUS FOR APPLYING LOCALIZED PRESSURE TO THE VENOUS SYSTEM OF THE LEG

(75) Inventor: Sundaram Ravikumar, Briarcliff Manor, NY (US)

(73) Assignee: Sun Scientific, Inc., Dobbs Ferry, NY (US)

( * ) Notice: Subject to any disclaimer, the term of this patent is extended or adjusted under 35 U.S.C. 154(b) by 20 days.

(21) Appl. No.: 11/050,104

(22) Filed: Jan. 24, 2005

(65) Prior Publication Data

US 2005/0131321 A1 Jun. 16, 2005

Related U.S. Application Data

(63) Continuation-in-part of application No. 10/400,901, filed on Mar. 27, 2003.

(51) Int. Cl.
*A61F 5/00* (2006.01)
*A61F 5/37* (2006.01)

(52) U.S. Cl. .......................................... 602/13; 602/54

(58) Field of Classification Search ................. 602/13, 602/75, 79, 54–57, 53, 14, 5, 1, 42, 41, 60, 602/19, 27, 23, 65, 63, 62, 61; 601/151, 601/152, 148, 149–150
See application file for complete search history.

(56) References Cited

U.S. PATENT DOCUMENTS

| | | | |
|---|---|---|---|
| 2,493,406 A | | 1/1950 | Hicks |
| 3,171,410 A | * | 3/1965 | Towle, Jr. et al. ............. 602/53 |
| 3,548,819 A | * | 12/1970 | Davis et al. .................... 602/14 |
| 3,561,435 A | * | 2/1971 | Nicholson .................... 602/14 |
| 3,633,567 A | * | 1/1972 | Sarnoff ........................ 600/499 |
| 3,901,225 A | * | 8/1975 | Sconce ......................... 602/13 |
| 4,029,087 A | | 6/1977 | Dye et al. |

(Continued)

OTHER PUBLICATIONS

"Summary of Safety and Effectiveness, Sensa-Cuff", GE Medical Systems Information Technologies, General Electric Company, Tampa, FL, Jun. 24, 2002.

(Continued)

*Primary Examiner*—Patricia Bianco
*Assistant Examiner*—Huong Q. Pham
(74) *Attorney, Agent, or Firm*—Gordon & Jackson, PC

(57) ABSTRACT

An apparatus is provided for applying compression therapy to an extremity of the human body, such as a portion of the human leg. The device includes a flexible member and an air bladder chamber. The flexible member is adapted to wrap around the extremity to secure the air bladder chamber to the extremity. An air pumping mechanism is operated to inflate the air bladder chamber to a pressurized state. One or more fluid-filled pressurized members are provided, each separate and distinct from the flexible member and the air bladder chamber and thus readily moveable relative to the flexible member and the air bladder chamber. The pressurized member(s) is operably disposed between the extremity and the flexible member whereby it applies increased localized pressure to the extremity during use. Preferably, the air bladder chamber is substantially longer in a first dimension than in a second dimension orthogonal thereto such that it can extend longitudinally along the extremity to cover a relatively long and narrow portion of the extremity. The position of the air chamber can be readily adapted to apply local pressure to desired body parts (such as certain venous channel). The pressurized member(s) can be positioned during use such that it covers a venous ulcer (or other treatment sites) and applies increased localized pressure to the treatment site in order to promote healing.

35 Claims, 7 Drawing Sheets

U.S. PATENT DOCUMENTS

| | | | |
|---|---|---|---|
| 4,091,804 A | | 5/1978 | Hasty |
| 4,207,876 A | | 6/1980 | Annis |
| 4,224,945 A | * | 9/1980 | Cohen .................. 606/201 |
| 4,269,175 A | | 5/1981 | Dillon |
| 4,396,010 A | | 8/1983 | Arkans |
| 4,941,458 A | * | 7/1990 | Taheri .................. 601/152 |
| 5,031,604 A | | 7/1991 | Dye |
| 5,042,496 A | | 8/1991 | Sjonell |
| 5,047,285 A | * | 9/1991 | Ward .................... 442/185 |
| 5,170,781 A | | 12/1992 | Loomis |
| 5,172,689 A | * | 12/1992 | Wright ................. 607/104 |
| 5,179,941 A | | 1/1993 | Siemssen et al. |
| 5,330,452 A | * | 7/1994 | Zook ..................... 604/307 |
| 5,376,067 A | | 12/1994 | Daneshvar |
| 5,389,066 A | * | 2/1995 | Rhame, Jr. ............... 602/74 |
| 5,407,421 A | * | 4/1995 | Goldsmith ................ 602/5 |
| 5,411,518 A | * | 5/1995 | Goldstein et al. ......... 606/202 |
| 5,411,541 A | * | 5/1995 | Bell et al. .............. 607/104 |
| 5,419,757 A | | 5/1995 | Daneshvar |
| 5,437,610 A | | 8/1995 | Cariapa et al. |
| 5,443,440 A | | 8/1995 | Tumey et al. |
| 5,486,194 A | | 1/1996 | Kawasaki et al. |
| 5,507,721 A | | 4/1996 | Shippert |
| 5,514,155 A | | 5/1996 | Daneshvar |
| 5,520,630 A | * | 5/1996 | Daneshvar ................ 602/60 |
| 5,591,200 A | | 1/1997 | Cone et al. |
| 5,626,556 A | | 5/1997 | Tobler et al. |
| 5,711,760 A | | 1/1998 | Ibrahim et al. |
| 5,746,213 A | * | 5/1998 | Marks .................... 600/499 |
| 5,843,018 A | * | 12/1998 | Shesol et al. ............. 602/79 |
| 5,891,074 A | | 4/1999 | Cesarczyk |
| 5,916,183 A | | 6/1999 | Reid |
| 6,007,559 A | | 12/1999 | Arkans |
| 6,074,356 A | * | 6/2000 | Starkey et al. ............ 602/75 |
| 6,315,745 B1 | * | 11/2001 | Kloecker ................. 602/13 |
| 6,371,933 B1 | | 4/2002 | Gardon-Mollard |
| 6,384,294 B1 | | 5/2002 | Levin |
| 6,416,534 B1 | * | 7/2002 | Montagnino et al. ....... 607/114 |
| 6,436,064 B1 | | 8/2002 | Kloecker |
| 6,478,757 B1 | | 11/2002 | Barak |
| 6,488,643 B1 | | 12/2002 | Tumey et al. |
| 6,537,298 B2 | * | 3/2003 | Dedo .................... 606/203 |
| 6,712,780 B2 | * | 3/2004 | Darcey .................... 602/8 |
| 6,762,337 B2 | * | 7/2004 | Boukanov et al. .......... 602/53 |
| 2001/0020176 A1 | | 9/2001 | Mach |
| 2002/0062096 A1 | | 5/2002 | Bennett |
| 2003/0060845 A1 | | 3/2003 | Gardon-Mollard |
| 2003/0139696 A1 | | 7/2003 | Boukanov et al. |
| 2003/0199922 A1 | * | 10/2003 | Buckman ................. 606/202 |
| 2003/0203012 A1 | | 10/2003 | Serafica et al. |
| 2004/0024322 A1 | | 2/2004 | Caspers |
| 2004/0028739 A1 | | 2/2004 | Rippon et al. |
| 2004/0068290 A1 | | 4/2004 | Bates et al. |
| 2004/0111048 A1 | | 6/2004 | Jensen et al. |
| 2004/0193084 A1 | | 9/2004 | Ravikumar |
| 2004/0193103 A1 | | 9/2004 | Kumar |
| 2004/0236261 A1 | | 11/2004 | McCarthy et al. |
| 2005/0187501 A1 | * | 8/2005 | Ravikumar ............... 601/152 |

OTHER PUBLICATIONS

"Venous Ulcers"; ABC of Vascular Disease; S.R. Dodds, 2001; downloaded from Internet; www.simondodds.com/venus_ulcer; Dec. 31, 2004.

"Venous Sin Ulcers"; WebMD Health; topic overview; downloaded from Internet; www.webmd.com; Dec. 31, 2004.

* cited by examiner

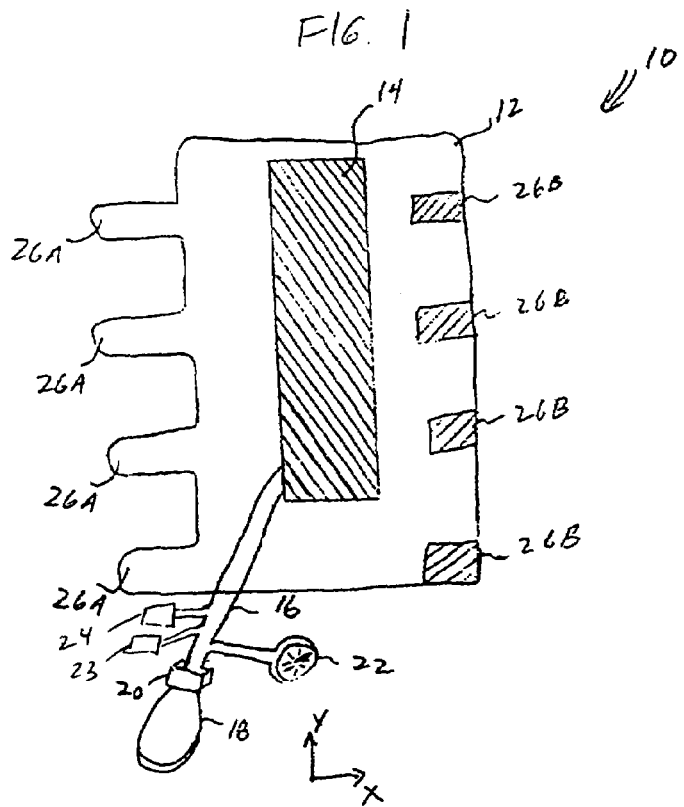
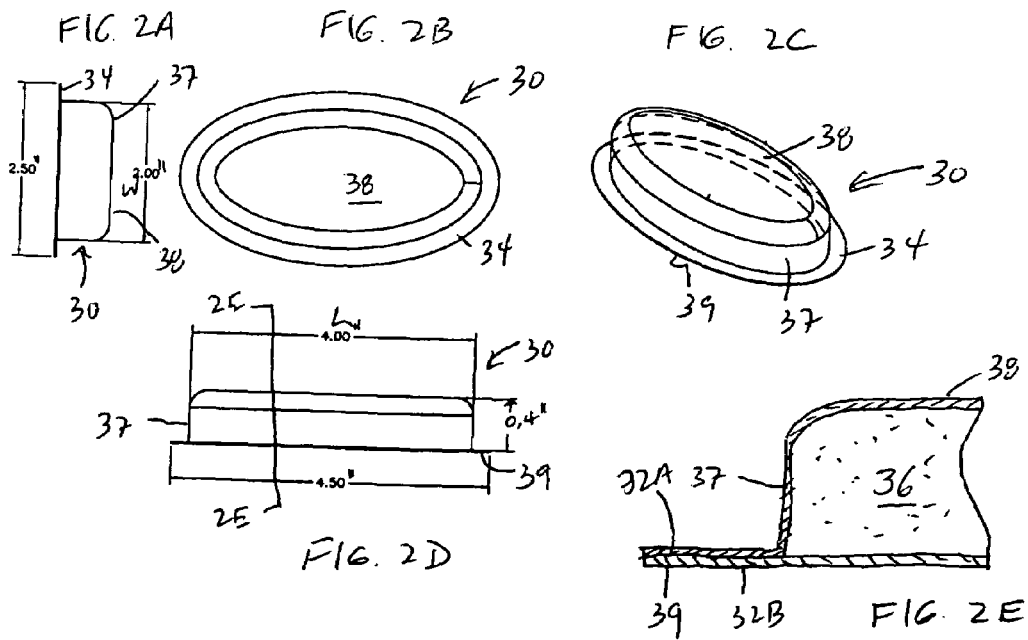

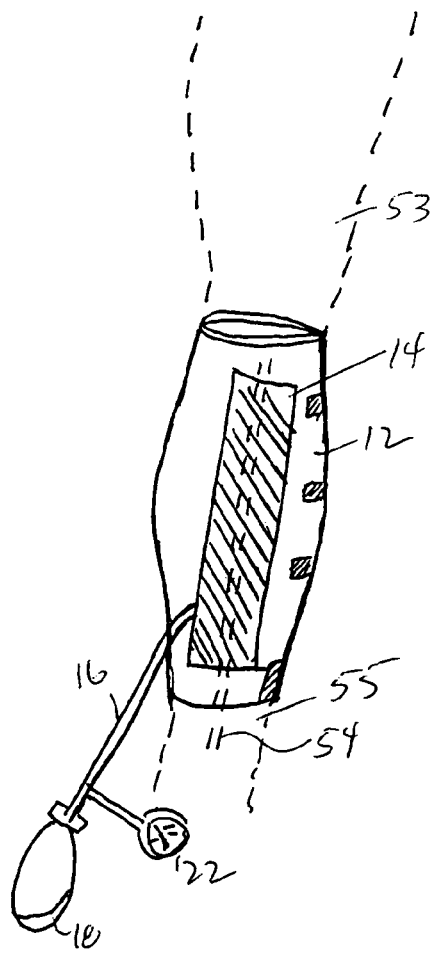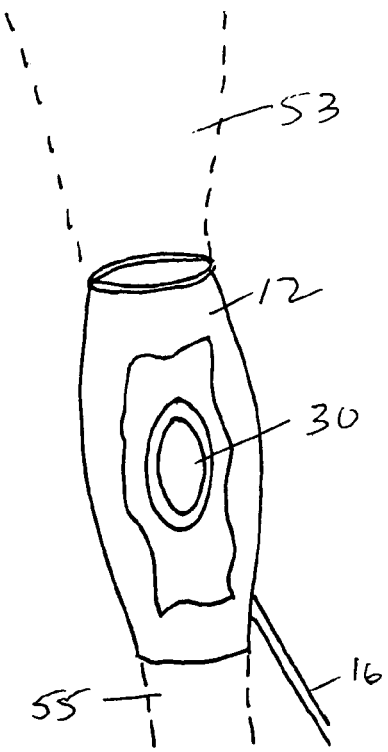
FIG. 3A
FIG. 3B

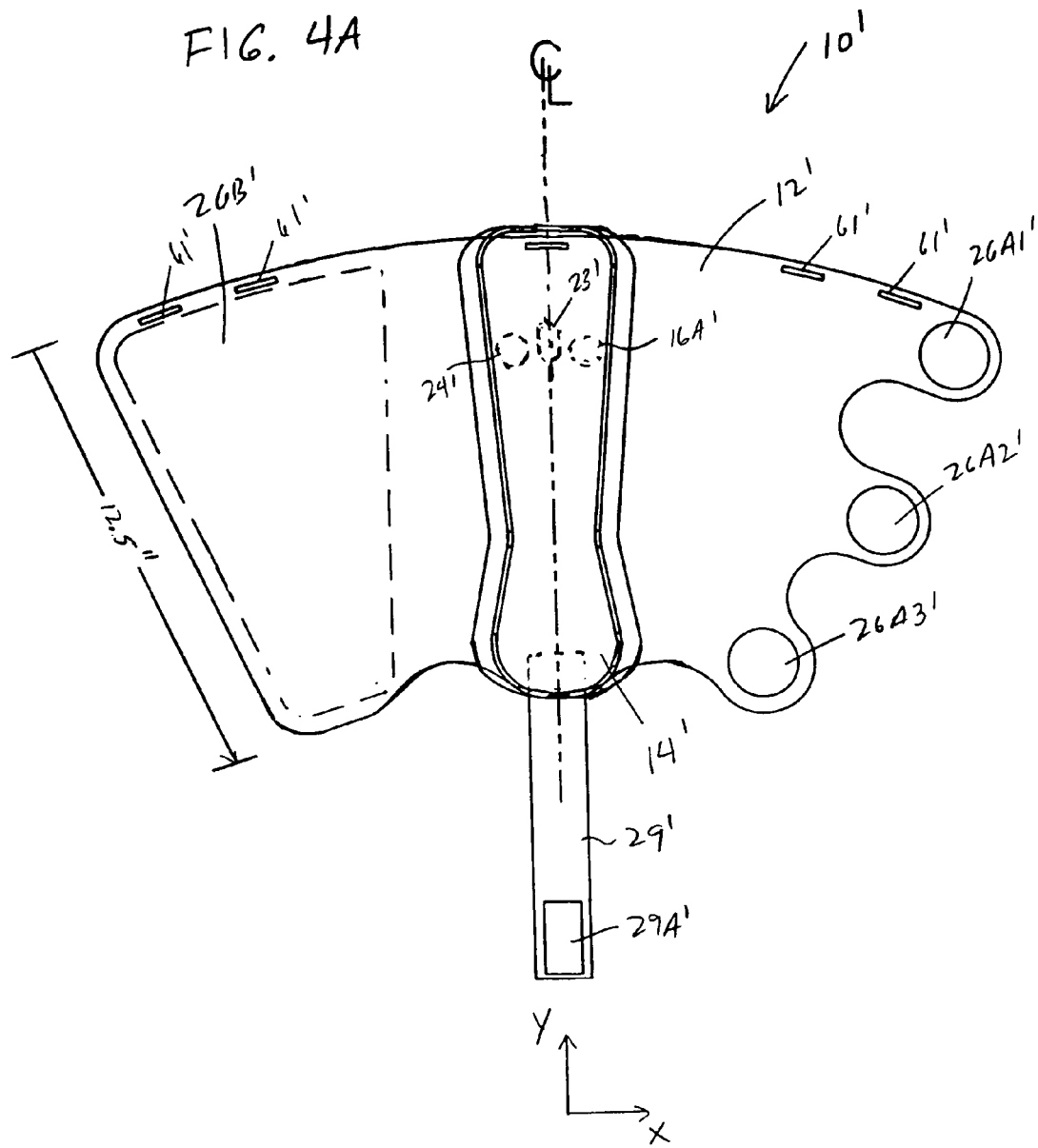

FIG. 4B
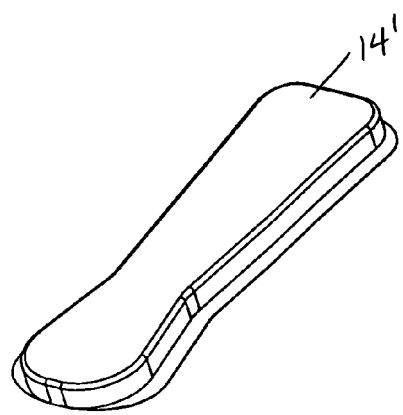
FIG. 4C
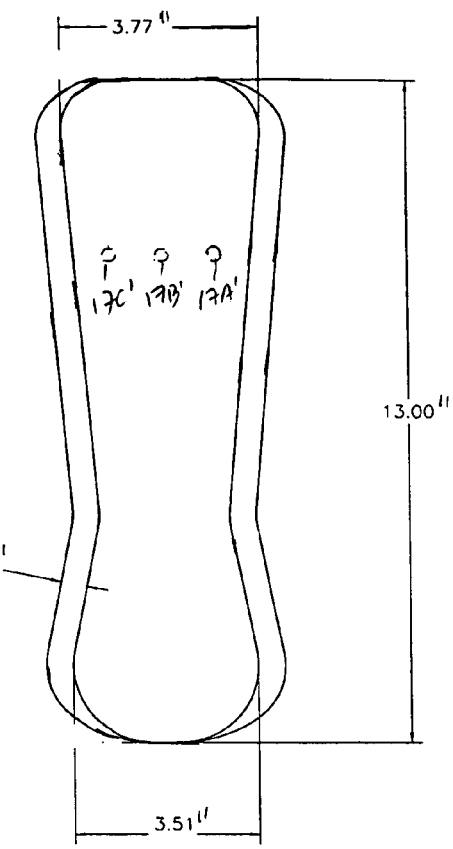
FIG. 4D
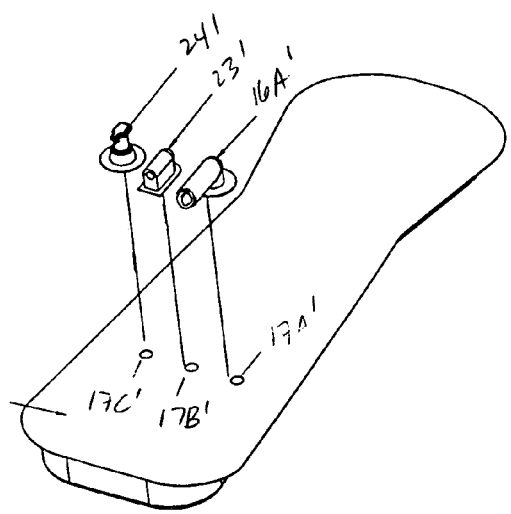
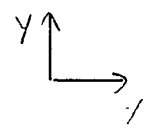

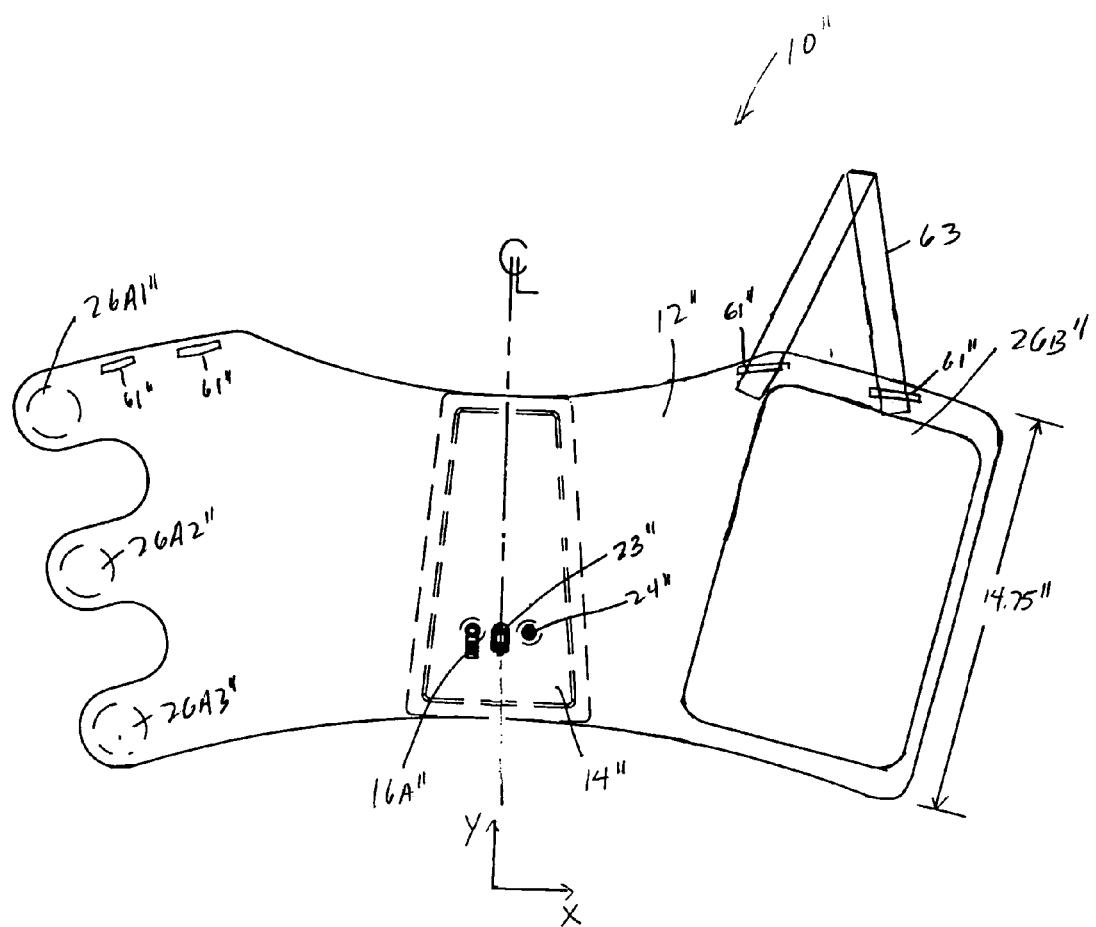

COMPRESSION APPARATUS FOR APPLYING LOCALIZED PRESSURE TO THE VENOUS SYSTEM OF THE LEG

CROSS-REFERENCE TO RELATED APPLICATIONS

The present application is a continuation-in-part of U.S. patent application Ser. No. 10/400,901 filed Mar. 27, 2003, commonly assigned to assignee of the present invention, herein incorporated by reference in its entirety.

BACKGROUND OF THE INVENTION

1. Field of the Invention

This invention relates to medical apparatus. More particularly, this invention relates to mechanisms for applying pressure to a leg of the human body in conjunction with the treatment of venous ulcers of the leg and possibly with other forms of medical treatment (e.g., sclerotherapy or vein stripping/removal for treatment for varicose veins) of the leg or other extremity.

2. State of the Art

A venous ulcer is damage and loss of skin above the ankle that is the result of a problem with the veins in the leg. Venous ulcers typically develop on either side of the lower leg, above the ankle and below the calf. They are difficult to heal and often recur.

The veins of the leg are divided into the superficial and deep systems according to their position relative to the fascia.

The deep veins, which come together to form the popliteal and femoral veins lie within the fascia and are responsible for the venous return from the leg muscles. Dilated valve less sinusoids also lie within the fascia (more particularly in the soleus and gastrocnemius muscles). The sinusoids fill with blood when the leg is at rest.

The long saphenous vein which runs along the medial side of the leg from foot to groin and the short saphenous vein which runs at the back of the calf from foot to knee are the major vessels of the superficial venous system. These vessels lie outside the fascia and are responsible for the venous return from the skin and subcutaneous fat.

Communicating veins, sometimes called perforators because they perforate the deep fascia, join the two systems. The perforators, like the other veins in the leg, contain valves that permit the flow of blood in one direction only, from the outer or superficial system inwards to the deep veins.

The venous pressure at the ankle of a subject who is lying supine is around 10 mmHg, but on standing this will rise considerably due to an increase in hydrostatic pressure (equivalent to the weight of a vertical column of blood stretching from the point of measurement to the right auricle of the heart).

During walking, as the foot is dorsally flexed, the contraction of the calf muscle compresses the deep veins and soleal sinuses thereby emptying them of blood. As the foot is plantarly flexed, the pressure in the veins falls, the proximal valves close, and the veins are refilled by blood passing through the perforators from the superficial system. During this cycle, in a normal leg, the distal valves of the deep veins and the valves of the perforators will ensure that the expelled blood can go in only one direction—upwards, back to the heart.

Blockage or damage to the venous system will cause disruption to normal blood flow, which may manifest itself in a number of different ways according to the site and extent of the damage. If the valves in the superficial system are affected, venous return will be impaired and blood may accumulate in the veins causing them to become distended, leading to the formation of varicosities (varicose veins).

If the function of the perforator valves is impaired, the action of the calf muscle pump will tend to cause blood to flow in the reverse direction into the superficial system increasing the possibility of damage to the superficial vessels.

Following a deep vein thrombosis that results in complete or partial obstruction of a deep vein, the unrelieved pressure produced by the calf muscle pump on the perforator valves may cause these to become incompetent. In this occurs, there will be a large rise in the pressure in the superficial system, which may force proteins and red cells out of the capillaries and into the surrounding tissue. Here, the red cells break down releasing a red pigment that causes staining of the skin, an early indicator of possible ulcer formation.

Venous leg ulcers are generally shallow and red in color. The skin surrounding the ulcer is frequently discolored due to the staining described previously. Incompetent perforating vein valves can also cause malleolar venules to become dilated and appear as fine red threads around the ankle. This condition, called ankle flair, is also diagnostic of a venous ulcer.

For patients with venous disease, the application of external compression can help to minimize or reverse the skin and vascular changes described previously, by forcing fluid from the interstitial spaces back into the vascular and lymphatic compartments. As the pressure within the veins of a standing subject is largely hydrostatic, it follows that the level of external pressure that is necessary to counteract this effect will reduce progressively up the leg, as the hydrostatic head is effectively reduced. For this reason it is usual to ensure that external compression is applied in a graduated fashion, with the highest pressure at the ankle. The preferred value for the degree of pressure varies according to a number of factors, including the severity of the condition and the height and limb size of the patient.

Medical hosiery represents a useful and convenient method of applying compression to normal shaped legs in order to prevent the development or recurrence of leg ulcers. However, these stockings are of limited value in the treatment of active ulceration, being difficult to apply over dressings. In such situations compression bandages currently represent the treatment of choice. Compression bandages apply a pressure to the limb that is directly proportional to bandage tension but inversely proportional to the radius of curvature of the limb to which it is applied. This means, therefore, that a bandage applied with constant tension to a limb of normal proportions will automatically produce graduated compression with the highest pressure at the ankle. This pressure will gradually reduce up the leg as the circumference increases.

As can be readily appreciated, it is cumbersome and difficult to apply uniform tension to the compression bandage as it is applied to the treated limb, and thus this is accomplished only by highly skilled caregivers. Moreover, once secured to the treated limb, care and attention must be given to ensure that the bandage does not slip or become displaced as this will lead to multiple layers forming, which in turn may lead to localized areas of high pressure, which can place the patient in direct risk of skin necrosis.

Mechanical compression treatments have also been proposed. An exemplary compression device is described in U.S. Pat. No. 5,031,604 to Dye. As generally described at col. 2, lines 33 et seq., an arrangement of chambers are provided that circumscribe the leg. An active pneumatic control system controls the pressure in the chambers to squeeze the leg near the ankle and then squeeze sequentially upward toward the knee in order to move blood from the extremity toward the heart. As noted in col. 4, lines 20-59 of U.S. Pat. No. 6,488,643 to Tumey et al., the mechanically produced compression levels may produce ischaemic (i.e., localized tissue anemia) not noted at similar compression levels obtained through bandaging. It may also produce cuffing (i.e., a reduction in leg pulsatile blood flow). The pneumatic control system is also bulky and heavy, which severely limits the mobility of the patient during treatment. Moreover, the pneumatic control system fails to provide a mechanism to ensure that excessive pressure, which can cause necrosis, is not applied to the treated limb. These limitations have resulted in most mechanical compression devices being contraindicated for patients exhibiting deep-vein thrombosis. Consequently, those skilled in the art have to date avoided such mechanical compression devices for the treatment of venous ulcers or edema of the extremities.

Thus, there are many problems, obstacles and challenges associated with the current treatments of leg ulcers and there is a need in the art to provide an apparatus for the treatment of venous ulcers (or an adema or other wound of the leg) that is simple to use, that is sure to produce the desired treatment, and that does not severely limit the mobility of the patient.

SUMMARY OF THE INVENTION

It is therefore an object of the invention to provide an apparatus for compression therapy that is easy to use and provides accurate and adjustable control over the pressure applied to the treated areas of a human limb.

It is another object of the invention to provide such an apparatus that is slim and lightweight and thus does not severely limit the mobility of the patient during treatment.

It is a further object of the invention to provide an apparatus that ensures that excessive pressure, which can cause necrosis, is not applied to the treated limb.

It is another object of the invention to provide such an apparatus that can be used to effectively apply pressure to the treated areas of the leg in conjunction with treatment of varicose veins in the limb over a wide range of patients and symptoms.

In accord with these objects, which will be discussed in detail below, an apparatus is provided for applying compression therapy to an extremity of the human body, such as a portion of the human leg. The device includes a flexible member and an air bladder chamber. The flexible member is adapted to wrap around the extremity to secure the air bladder chamber to the extremity. An air pumping mechanism is operated to inflate the air bladder chamber to a pressurized state. One or more fluid-filled pressurized members are provided, each separate and distinct from the flexible member and the air bladder chamber and thus readily moveable relative to the flexible member and the air bladder chamber. The pressurized member(s) is operably disposed between the extremity and the flexible member whereby it applies increased localized pressure to the extremity during use. The position of the air chamber can be readily adapted to apply local pressure to desired body parts (such as certain venous channel). The pressurized member(s) can be positioned during use such that it covers a venous ulcer (or other treatment sites) and applies increased localized pressure to the treatment site in order to promote healing. According to one embodiment of the invention, the air bladder chamber is substantially longer in a first dimension than in a second dimension orthogonal thereto such that it can extend longitudinally along the extremity to cover a relatively long and narrow portion of the extremity. When the flexible member and air bladder chamber are securely held over the long narrow portion of the leg and the air bladder chamber is inflated to the desired pressure, local pressure is applied to the long narrow leg portion. Such local pressure is useful in conjunction with treatment of varicose veins in specific areas of the lower leg as described herein.

According to a preferred embodiment of the present invention, the air pumping mechanism of the device comprises a pumping bulb and valve that are manually manipulated to inflate the air bladder chamber.

According to yet another embodiment of the invention, the device includes a pressure gauge in fluid communication with the air bladder chamber, which provides a visual indication of pressure levels within the air bladder chamber.

Additional objects and advantages of the invention will become apparent to those skilled in the art upon reference to the detailed description taken in conjunction with the provided FIGS.

BRIEF DESCRIPTION OF THE DRAWINGS

FIG. 1 is an isometric view of a pneumatic compression mechanism in accordance with the present invention, showing the mechanism in its unwrapped state.

FIGS. 2A-2E are views of a fluid-filled member that is used in conjunction with the bladder-based compression mechanism of FIG. 1 to apply increased localized pressure to a venous ulcer (or to some other type of treatment site such as an adema or wound) in accordance with the present invention; FIG. 2A is a side view of the fluid-filled member; FIG. 2B is a top view of the fluid-filled member; FIG. 2C is a perspective view of the fluid-filled member; FIG. 2D is a front view of the fluid-filled member of FIG. 2A; and FIG. 2E is a partial cross-section schematic view of the fluid-filled member showing fluid therein.

FIGS. 3A and 3B are views of the pneumatic compression mechanism of FIG. 1 and the fluid-filled member of FIGS. 2A-2D, showing the compression mechanism securely wrapped around the lower leg of a human patient and enveloping the fluid-filled member; FIG. 3A shows the air bladder of the compression mechanism disposed along the calf of the leg for applying pressure to short saphenous vein of the lower leg; and FIG. 3B shows the fluid-filled member covering a venous ulcer disposed on the tibia of the lower leg for applying increased localized pressure to the venous ulcer.

FIG. 4A is a view of an embodiment of a pneumatic compression mechanism in accordance with the present invention; the compression mechanism is intended to be wrapped around the lower leg for application of localized pressure to the lower leg in the vicinity of the short saphenous vein; the compression mechanism is shown in its unwrapped state with its body-contacting surface facing out of the page.

FIG. 4B is an isometric view of the air bladder chamber of the pneumatic compression mechanism of FIG. 4A.

FIG. 4C is a top view of the air bladder chamber of FIG. 4B.

FIG. 4D is an exploded view showing the coupling of valve elements and a connector to the air bladder chamber of FIGS. 4B and 4C.

FIG. 5A is a view of an embodiment of a pneumatic compression mechanism in accordance with the present invention; the compression mechanism is intended to be wrapped around the upper leg (e.g., thigh) for application of localized pressure to the upper leg in the vicinity of the long saphenous vein; the compression mechanism is shown in its unwrapped state with its body-contacting surface facing into the page.

DETAILED DESCRIPTION OF THE PREFERRED EMBODIMENTS

Figure 5B:
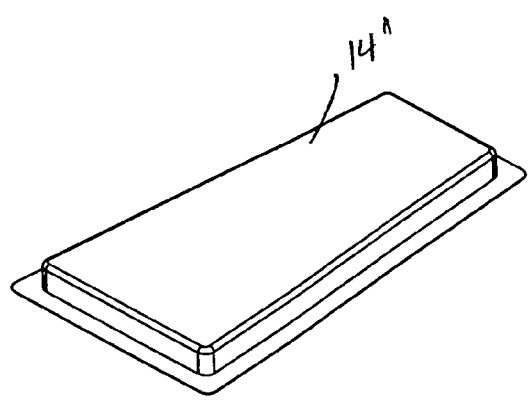
FIG. 5B is an isometric view of the air bladder chamber of the pneumatic compression mechanism of FIG. 5A.
Figure 5C:
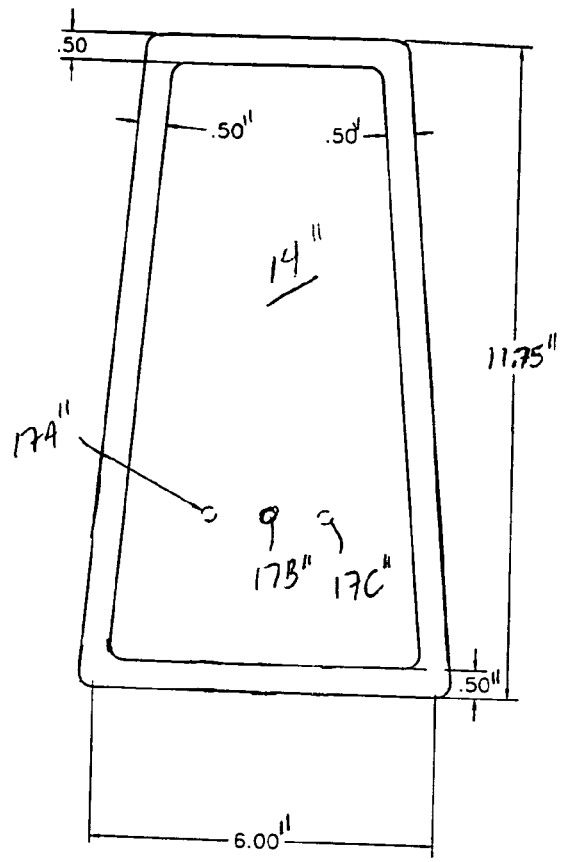
FIG. 5C is a top view of the air bladder chamber of FIG. 5B.
Figure 5D:
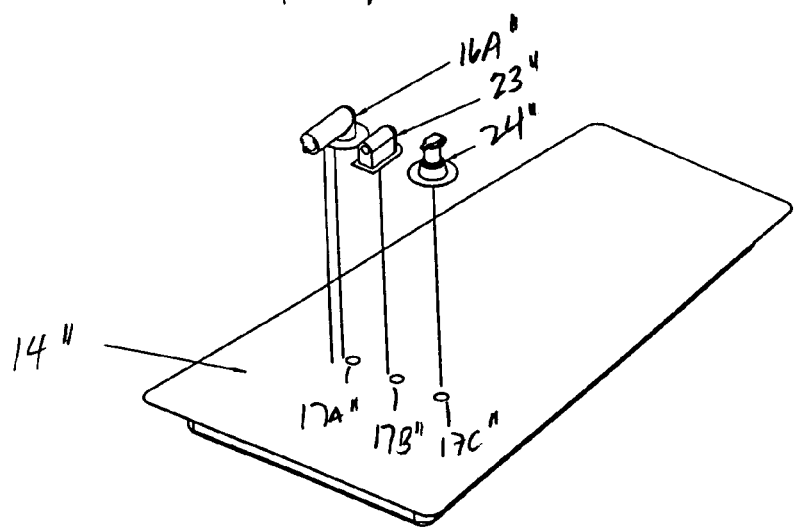
FIG. 5D is an exploded view showing the coupling of valve elements and a connector to the air bladder chamber of FIGS. 5B and 5C.

Turning now to FIG. 1, a pneumatic compression mechanism is provided for applying pressure to the lower leg of the human body. The pneumatic compression mechanism 10 includes a flexible member 12 and one or more inflatable air bladder chambers 14 (preferably, a single air bladder as shown). The inflatable air bladder chamber 14 is preferably secured to the flexible member 12 in its unwrapped state. For example, the flexible member 12 may comprise two layers of elastomeric material with the air bladder chamber(s) 14 affixed between these two layers by nylon threads or other suitable fastening means. Alternatively, the flexible member 12 may include pockets into which the air bladder chamber(s) 14 are removably inserted and securely held therein. In yet another alternative embodiment, the air bladder may be glued or welded to the inside surface of the member 12. The elastomeric material of the member 12 may be realized from nylon, polyurethane, cotton, or other suitable material. A tube 16, which is in fluid communication with the air bladder chamber(s) 14, extends to a pumping bulb 18. The pumping bulb 18, which is preferably made of rubber, includes a valve 20 that regulates the pumping of air into the air bladder chamber(s) 14 via the tube 16. Air is pumped into the air bladder chamber(s) 14 by squeezing the pumping bulb 18. In this manner, the air bladder chamber(s) 14 are placed into a pressurized state. Preferably, a pressure gauge 22 is operably coupled to the air bladder chamber(s) 14 to provide a visual indication of the pressure level therein. An automatic pressure relief valve 23 and a manual pressure relief valve 24 may be operably coupled to the air bladder chamber(s) 14, for example via the tube 16. The automatic pressure relief valve 23 automatically vents the air in the chamber(s) 14 to the ambient environment when the internal pressure reaches a certain threshold maximum pressure. In the preferred embodiment, this threshold maximum pressure is between 30 to 40 mmHg, and most preferably around 40 mmHg; however it can be varied based upon the desired treatment. In this manner, the pressure inside the chamber(s) 14 cannot exceed the threshold maximum pressure, thereby reducing the danger of necrosis and other complications that arise from excessive pressure. The manual pressure relief valve 24 vents the air in the chamber(s) 14 to the ambient environment when manually actuated by the patient (or caregiver). In this manner, it facilitates quick and easy control over the internal pressure of the air chamber(s) 14. In alternative embodiments, the manual pressure relief valve 24 and possible the automatic relief valve 23 may be integrated into a common package.

The air bladder chamber 14 is substantially longer in a first dimension (e.g., the Y dimension of FIG. 1) than in a second dimension orthogonal thereto (e.g., the X dimension of FIG. 1) such that the air bladder chamber 14 can be positioned to extend substantially longitudinally along the lower leg to apply local pressure along its length (the Y dimension). Such local pressure is substantially constant along the length of the bladder chamber 14. In the illustrative embodiment shown in FIGS. 3A and 3B, the air bladder chamber 14 is disposed such that it runs along the calf of the lower leg, which enables the air bladder chamber 14 to apply local pressure to the short saphenous vein of the patient when securely wrapped around the patient's lower leg and inflated. However, the flexible member 12 and air bladder chamber 14 may be adapted such that they are disposed along another portion of the lower leg (e.g., a portion of the leg below the knee), which enables the air bladder chamber 14 to apply local pressure to such portion of the lower leg when inflated.

The flexible member 12 may include a strap (not shown) that extends around the heal (and/or other parts) of the foot when in use. This strap limits the upward travel of the flexible member 12 when in use. It may also have suspender hooks or slots (not shown) that allow for suspenders to be mated thereto which support the mechanism 10 by a band that wraps around the knee or thigh. The suspenders limit downward travel of the flexible member 12 when in use. These features reduce the travel of the flexible member 12 along the length of the leg such that its desired position is maintained during use.

In alternative embodiments, the flexible member 12 and air bladder chamber 14 may be adapted such that they are disposed along a portion of the upper leg (e.g., a portion of the thigh), which enables the air bladder chamber 14 to apply local pressure to such portion of the upper leg when inflated. For treatment of the upper leg, the flexible member 12 may define an opening (not shown) at the knee joint level to enable the patella (knee cap) to protrude therethrough. In this configuration, the flexible member 12 may extend below the knee joint level and securely wraps around portions of the lower leg to provide stability to the leg. It may also have suspender hooks or slots (not shown) that allow for suspenders to be mated thereto in order to support the mechanism 10 by a waist band when in use. The suspenders limit downward travel of the flexible member 12 when in use such that the flexible member 12 maintains its desired position.

Preferably, the flexible member 12 includes multiple hook and loop closure mechanisms 26A, 26B (e.g., VELCRO® members). In the preferred embodiment, the flexible member includes four hook and loop closure mechanisms as shown in FIGS. 1 through 3A. These multiple closures enable the flexible member 12 and the air bladder chamber(s) 14 to be securely wrapped around a portion of the human leg. If desired, other suitable fastening means may be used to secure the flexible member and the air bladder chamber(s) to the human leg. For example, the flexible member may be adapted to form a sleeve-like shape with a zipper running along its length dimension. Alternatively, the zipper may be omitted such that sleeve-like flexible member is slid over the patient's leg until it is disposed in the desired position.

Preferably, pressure in the air bladder chamber(s) is reduced/removed (e.g., the air bladder chamber(s) are deflated) by user manipulation of the manual relief valve 24, and the pneumatic compression mechanism is removed from the leg by manually detaching the hook and loop closures and unwrapping the flexible member 12 from around the leg.

FIGS. 2A-2E illustrate a fluid-filled member 30 that is used in conjunction with the pneumatic compression mechanism 10 of FIG. 1 to apply increased localized pressure to a venous ulcer (or to some other type of treatment site such as an adema or wound). The fluid-filled member 30 includes two walls 32A, 32B (FIG. 2E) that are bonded together, preferably by heat sealing, about a flange portion 34. The two walls 32A, 32B define a chamber 36 therebetween that is filled with fluid. The top wall 32A extends orthogonally from the flange portion 34 to form a small sidewall section 37 and then curves to form a top section 38. The top section 38 is operably disposed adjacent the flexible member 12 of the compression member 10, while the bottom wall 32B is operably disposed adjacent the treatment site as described below.

The fluid held in the chamber 36 can be a gas (such as air), a liquid (such as water), or a gel. The underside surface 38 of the flange portion 34 preferably includes a peel-off adhesive film that aids in securing the member 30 to the skin (or possibly to the flexible member 12 and/or to the air bladder 14) at the treatment site. The fluid inside the chamber 36 may be loaded with one or more therapeutic agents, such as antibiotics, growth factor, absorbents. In such configurations, the bottom wall 32B is realized from a semi-permeable material that allows the therapeutic agents retained in the chamber 36 to migrate through to the treatment site while maintaining the desired internal pressure in chamber 36. Such fluid might also be a gel compound that retains heat and/or cold such that is useful for hot and/or cold therapy of the treatment site.

The fluid-filled member 30 preferably has an oval shape with a length on the order of 4 inches (with a 0.25 inch wide flange), a width on the order of 2 inches, and a height on the order of 0.75 inches as shown in FIGS. 2A-2D. It will be appreciated that the fluid-filled member 30 may take other shapes and sizes.

The pneumatic compression mechanism of FIG. 1 and the fluid-filled member of FIGS. 2A-2E are used to apply pressure to the lower leg during treatment. For example, FIG. 3A shows the air bladder 14 of the compression mechanism 10 disposed along the calf 51 of the leg 53 for applying pressure to short saphenous vein (shown as dotted line pair 54) of the lower leg 55. FIG. 3B shows one fluid-filled member 30, which is disposed in the cutaway portion under the flexible member 12, covering a venous ulcer (not shown) disposed on the tibia of the lower leg 55. In this configuration, the fluid-filled member 30 is placed over the treatment site (i.e., the venous ulcer). It is enveloped by wrapping the flexible member 12 around the lower leg 55 with the air bladder chamber(s) 14 disposed along the calf 50 of the leg as shown in FIG. 3A. Pressure is applied to the air bladder chamber(s) 14 by manipulating the pumping bulb 18 until the air bladder chamber(s) is (are) inflated to a desired target pressure, preferably on the order of 40-80 mmHg. Preferably, this target pressure level is visually indicated on the pressure gauge 22. The local pressure applied by the inflated air bladder chamber 14 is substantially constant along the length of the bladder chamber 14. The fluid-filled member 30 applies increased and more localized pressure to its treatment site, which is expected to aid in the healing of the treatment site.

The pneumatic compression mechanism of FIG. 1 and one or more fluid-filled members of FIGS. 2A-2E can be used in conjunction with vein ligation and/or surgical vein stripping, whereby pressure is applied to the treated venous channels by the air bladder of the pneumatic compression mechanism. In this application, the air bladder chamber applies local pressure to the treatment area to control bleeding that results from this procedure. Such local pressure is substantially constant along the length of the bladder chamber. The fluid-filled member(s) applies increased and more localized pressure over a venous ulcer (or other treatment site). Similarly, when used in conjunction with sclerotherapy, the air bladder chamber applies local pressure to the treatment area to significantly reduce the amount of blood that pools (or might potentially flow back) into the treated venous channel. This enables the sclerosing agent to have maximum effect in destroying the venous channel in the treated area of the thigh. The fluid-filled member(s) may be positioned to cover one or more localized treatment sites (for example, over spider veins that are treated with scelrotherapy) to provide increased localized pressure to the treatment site(s) that promotes healing.

It is also contemplated that the patient may utilize the pneumatic compression mechanism of FIG. 1 and the fluid-filled members of FIGS. 2A-2E can be used in conjunction with saphenous vein harvesting. The long saphenous vein is typically used to bypass arterial blockages, to perform arterial bypass grafts and other cardiac procedures. Heparin is typically administered to the patient for anticoagulation purposes. However, the heparin also prevents clot formation in and around the area of the harvested vein, which may cause generalized bleeding or oozing to form a hematoma and possibly an infection or other complication. In this application, localized pressure is applied to the harvested venous channel by the air bladder of the pneumatic compression mechanism. Such local pressure is substantially constant along the length of the bladder chamber. The fluid-filled member applies increased and more localized pressure over the hematoma (or other treatment site such as in incision site) to promote healing.

Furthermore, it is contemplated that the patient may utilize the pneumatic compression mechanism of FIG. 1 and one or more of the fluid-filled members of FIGS. 2A-2E to apply increased and more localized pressure to the treated areas of the leg for an extended period of time (e.g., periods of days/weeks) subsequent to treatment.

It should be noted that amount of fluid that is added to the chamber 36 at the time it is filled and/or the volume of chamber 36 is fixed by design. These parameters dictate the internal pressure of the chamber 36. In other words, the internal pressure of the chamber 36 is static. However, by adjusting the amount of fluid added to the chamber 36 at fill time or by adjusting the volume of chamber 36 or by adjusting both parameters, the internal pressure of the chamber 36 can vary. More particularly, the internal pressure of chamber 36 is proportional to the amount of fluid added to the chamber 36 at fill time and inversely proportional to the volume of chamber 36. These relationships can be exploited to provide a set of fluid-filled members (30A, 30B, 30C . . . ) that have varying internal pressures. For, example, the fluid-filled members of the set can have the same volume but are filled with different amounts of fluid to provide the varying internal pressures. Alternatively, the fluid-filled members of the set can have different volumes that are filled with the same amount of fluid to provide the varying internal pressures. Preferably, the set of fluid-filled members and one or more pneumatic compression apparatus are packaged as a kit. The particular fluid-filled member that is expected to provide the desired increase in local pressure is selected from the set and used in conjunction with the pneumatic compression apparatus as described above. Trial and error may be used to identify the appropriate fluid filled member for the desired treatment.

Figure 6:
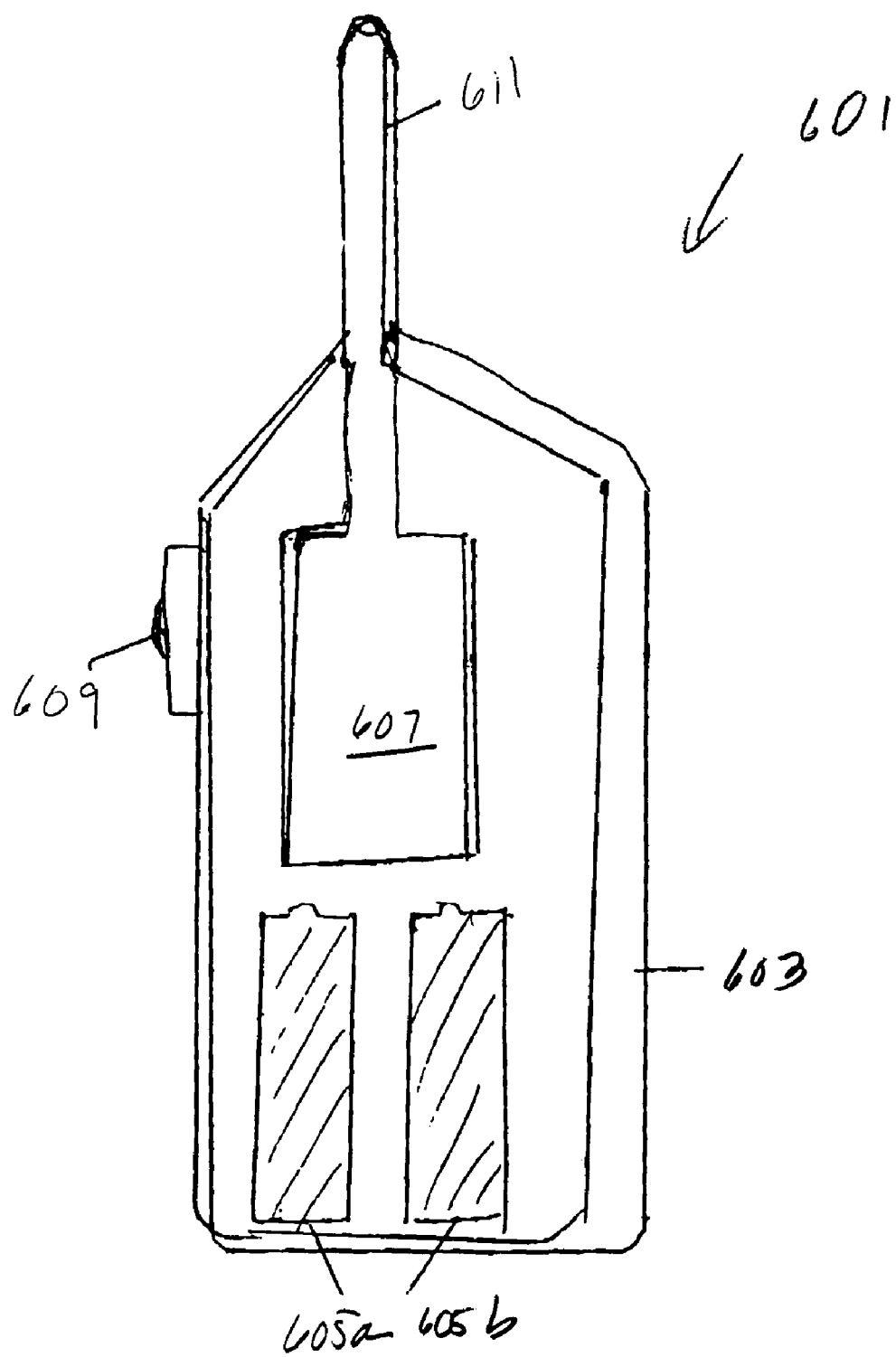
FIG. 6 is a schematic illustration of a battery-powered air pump suitable for inflating the air bladder chamber(s) of the pneumatic compression mechanisms described herein.

Turning now to FIGS. 4A-4D, an alternate embodiment of a pneumatic compression mechanism is shown. The pneumatic compression mechanism 10' includes a flexible member 12' and one or more inflatable air bladder chambers 14' (preferably, a single air bladder as shown). The inflatable air bladder chamber 14' may be formed from two walls that are bonded together, preferably by heat sealing, about a flange portion in a manner similar to the fluid-filled members 30 as described herein. The air bladder chamber 14' is secured to the inside surface of the flexible member 12' preferably by gluing, welding or other suitable fastening means. Alternatively, the flexible member 12' may comprise two layers of elastomeric material with the air bladder chamber(s) 14' affixed between these two layers by nylon threads or other suitable fastening means. The flexible member 12' is preferably realized from nylon, polyurethane, cotton, or other suitable material. A connector 16A' is in fluid communication with the air bladder chamber(s) 14' via a port 17A', which preferably extends through the bottom side of the air bladder chamber 14' as shown in FIG. 4D. The connector 16A' mates to an inflation tube (not shown) for fluid connection to the pumping bulb as described above or other inflation mechanisms (such as a battery-powered pump as shown in FIG. 6). An automatic pressure relief valve 23' and a manual pressure relief valve are in fluid communication with the air bladder chamber(s) 14' via ports 17B' and 17C', respectively, which preferably extend through the bottom side of the air bladder chamber(s) 14' as shown in FIG. 4D.

Preferably, the flexible member 12' includes multiple hook and loop closure mechanisms (e.g., VELCRO® members) which enable the flexible member 12' (and the air bladder chamber(s) 14' secured thereto) to be securely wrapped around a portion of the human leg. In the exemplary embodiment of FIGS. 4A-4D, the flexible member 12' includes three hook buttons 26A1', 26A2', 26A3' disposed on the body-contacting side of member 12' that mate to a larger loop panel section 28B' disposed on the opposite side of member 12'. If desired, other suitable fastening means may be used to secure the flexible member 12' and the air bladder chamber(s) 14' to the human leg. For example, the flexible member 12' may be adapted to form a sleeve-like shape with a zipper running along its length dimension. Alternatively, the zipper may be omitted such that sleeve-like flexible member 12' is slid over the patient's leg until it is disposed in the desired position. The flexible member 12' may also include cut-outs (not shown) which provide enhanced flexibility of the member 12'.

During use, air is pumped into the air bladder chamber(s) 14' by actuation of the pumping bulb (or other inflation mechanism). The air bladder chamber 14' is substantially longer in a first dimension (e.g., the Y dimension of FIGS. 4A and 4C) than in a second dimension orthogonal thereto (e.g., the X dimension of FIGS. 4A and 4X) such that the air bladder chamber 14' can be positioned to extend substantially longitudinally along the leg to apply local pressure along its length (the Y dimension). Such local pressure is substantially constant along the length of the bladder chamber 14'.

In the exemplary embodiment shown, the air bladder chamber 14' has a length of 13.00 inches (Y dimension) and width of 3.77 inches and 3.51 inches (X dimension) at its top and bottom ends, respectively, as shown. The width of the chamber 14' tapers as it extends away from the top and bottom ends to a minimal width, which is located relatively closer to the bottom end as shown. It will be appreciated that the air bladder chamber 14' may take other shapes and sizes.

One or more fluid-filled members 30 can be used in conjunction with the pneumatic compression mechanism 10' of FIGS. 4A-4D to apply increased localized pressure to a treatment site in a manner similar to those described above.

In an exemplary application, the air bladder chamber 14' is positioned such that that it runs along the calf of the lower leg and covers the short saphenous vein of the patient as shown in FIGS. 3A and 3B. It is secured in this position by wrapping the flexible member 12' around the lower leg and closing it with closure mechanisms 26A1', 26A2', 26A3' and 26B'. The air bladder chamber 14' is inflated to its desired pressure to apply local pressure to short saphenous vein of the patient. One or more fluid-filled members 30 can be positioned above treatment site(s) (e.g., a venous ulcer) before securing the flexible member 12' to the lower leg to apply increased and more localized pressure on the treatment site(s) to promote healing. After inflating the chamber 14' to its desired pressure, the inflation pump can be decoupled from the connector 16A' and replaced with a plug (not shown). The flexible member 12' includes a strap 29' that extends around the heal (and/or other parts) of the foot during use. A hook closure segment 29A' mates to loop panel section 26B' to secure the strap 29' around the foot. The strap 29' limits the upward travel of the flexible member 12' during use. The member 12' may also have one or more slots 61' (for example five shown) that allow for suspenders (not shown) to be mated thereto which support the mechanism 10' by a band that wraps around the knee or thigh. The suspenders limit downward travel of the member 12' when in use. Thus, the strap and the suspenders cooperate to reduce the travel of the flexible member 12' along the length of the leg such that its desired position is maintained during use.

In alternative embodiments as shown in FIGS. 5A-5D, a flexible member 12" and air bladder chamber 14" are adapted such that they are disposed along a portion of the upper leg (e.g., a portion of the thigh), which enables the air bladder chamber 14" to apply local pressure to such portion of the upper leg when inflated. The structure and operation of the elements of the mechanism 10" are analogous to the mechanism 10' as described above with respect to FIGS. 4A-4D, and thus description of such elements (which are labeled with like numbers) are omitted for simplicity of description.

In the exemplary embodiment shown, the flexible member 12" is contoured to conform to the upper leg when wrapped around it. The air bladder chamber 14" has a length of 11.75 inches (Y dimension) and maximum width of 6.00 inches (X dimension) at its bottom end as shown. The width of the chamber 14" tapers as it extends away from the bottom end to the top end as shown. It will be appreciated that the air bladder chamber 14" may take other shapes and sizes.

One or more fluid-filled members 30 can be is used in conjunction with the pneumatic compression mechanism 10" of FIGS. 5A-5D to apply increased localized pressure to a treatment site in a manner similar to those described above.

In an exemplary application, the chamber 14" is positioned such that that it runs along the thigh and covers the long saphenous vein of the patient. It is secured in this position by wrapping the flexible member 12" around the thigh and closing it with closure mechanisms 26A1", 26A2", 26A3" and 26B". The air bladder chamber 14" is inflated to its desired pressure to apply local pressure to long saphenous vein of the patient. One or more fluid-filled members 30 can be positioned above treatment site(s) (e.g., a venous ulcer) before securing the flexible member 12" to the upper leg in order to apply increased and more localized pressure on the treatment site(s) to promote healing. After inflating the chamber 14" to its desired pressure, the inflation pump can be decoupled from the connector 16A" and replaced with a plug (not shown). The flexible member 12" has suspender hooks or slots 61" as shown in FIG. 5A. The hooks or slots 61" allow for suspenders 63" to be mated thereto in order to support the mechanism 10" by a waist band when in use. The suspenders 63" limit downward travel of the flexible member 12" when in use such that the flexible member 12" maintains its desired position. The flexible member 12" may also define an opening (not shown) at the knee joint level to enable the patella (knee cap) to protrude therethrough. In this configuration, the flexible member 12' may extend below the knee joint level and securely wraps around portions of the lower leg to provide stability to the leg.

FIG. 6 illustrates a battery-powered air pump 601 suitable for inflating the air bladder chamber(s) of the pneumatic compression mechanisms described herein. The pump 601 includes a housing 603 that houses one or more batteries (two shown as 605a, 605b) that power a pneumatic air pump 607. An on/off switch 609, which is electrically coupled between the batteries and the air pump 607, that manually manipulated to control the supply of battery power to the air pump. When the switch 609 is ON, battery power is applied to the air pump such that it pumps air through a nozzle 611. The nozzle 611 is fluidly coupled to the air bladder chamber(s) of the pneumatic compression mechanisms described herein for inflation of such chamber(s).

Advantageously, the pneumatic compression mechanism and fluid-filled members of the present invention provide for accurate control and monitoring of localized pressure applied to the treated areas of a human leg. Moreover, they are simple to use, lightweight and flexible and thus do not significantly reduce the mobility of the patient. Finally, because the fluid-filled members are separate and distinct from the compression wrap, they can be positioned between the extremity and the wrap member at arbitrary locations. This flexibility allows for increased localized pressure to be applied over a wide range of locations on the extremity and thus allows the treatment to be more effectively tailored to the injuries/symptoms of the patient.

In alternate embodiments with respect to those described above, the member and the inflatable air bladder chamber may be adapted such that they are separate and distinct from one another and thus moveable relative to one another when the member is in its unwrapped state. This feature allows for flexibility in positioning of the air bladder chamber. This flexibility allows for the pressure therapy to be applied over a wide range of locations on the extremity and thus allows the treatment to be more effectively tailored to the injuries/symptoms of the patient.

There have been described and illustrated herein a preferred embodiment of an apparatus (and corresponding method of operation) that is secured to a portion of the human leg and controlled to apply localized pressure to portions of the human leg. While a particular embodiment of the invention has been described, it is not intended that the invention be limited thereto, as it is intended that the invention be as broad in scope as the art will allow and that the specification be read likewise. Thus, while particular fastening mechanisms and particular pressure control mechanisms have been disclosed, it will be appreciated that other suitable mechanisms that may be used as well. For example, the air pump mechanism may include an automatic air pumping mechanism (such as the battery-powered air pump of FIG. 6) rather than a hand-held manually actuated air pumping mechanism as described above. In addition, the air pump mechanism may be removably coupled to tubing that leads to the pressure valve and air chamber(s) of the device such that air pump mechanism can be disconnected from the device with the pressure valve closed (thereby maintaining the device in its pressurized state). Also, the pneumatic compression mechanism may extend to cover lower and/or higher portions of the leg than those shown. In yet alternative embodiments, the compression mechanisms can be used to apply localized pressure to other veins of the leg or to other extremities, such as the arm, for wound healing or other treatments. It will therefore be appreciated by those skilled in the art that yet other modifications could be made to the provided invention without deviating from its spirit and scope as claimed.

What is claimed is:

1. A system for applying external pressure to a saphenous vein of the human leg which extends longitudinally along the leg, the device comprising:
   a) a flexible member having an encircling configuration that wraps around the human leg and an opened unwrapped configuration, said encircling configuration defining a central axis therethrough, said flexible member having a first length in a direction of said central axis and said flexible member having a first width when in said opened unwrapped configuration;
   b) an elongate air bladder of a first size supported by said flexible member in said encircling configuration, said air bladder having a second length extending in said encircling configuration in a direction substantially parallel to the central axis and to said first length, and said elongate air bladder having a second width, said second length being at least twice said second width and said second width being less than half said first width, said air bladder capable of inflation to a pressurized state which supplies compressive forces that are directed radially inward toward the central axis and adapted due to said second length and second width to apply said compressive forces to the saphenous vein of the leg when supported by said flexible member in said encircling configuration;
   c) an air pumping mechanism, operably coupled to said air bladder, that operates to inflate said air bladder to a pressurized state that is less than 40 mmHg, whereby in the pressurized state said air bladder provides for application of external pressure to the saphenous vein of the leg that is covered by said air bladder; and
   d) at least one pressurized member of a second size less than one-half said first size and having a sealed chamber filled with fluid to a pressurized state, said pressurized member separate and distinct from said flexible member and said air bladder and thus moveable relative to said flexible member and air bladder, said pressurized member having means for adhering said pressurized member to the leg such that it is operably disposed between the leg and the flexible member whereby it applies increased localized pressure to the leg.

2. A system according to claim 1, wherein:
   said pressurized member has peripheral portion having said means for adhering said pressurized member to the leg.

3. A system according to claim 2, wherein:
   said means for adhering comprises a peel-off adhesive strip suitable for adhering to the skin.

4. A system according to claim 2, wherein:

said pressurized member comprises two walls that are joined together at their periphery to form a flange, said flange comprising said peripheral portion.

5. A system according to claim 4, wherein:

said two walls define the sealed chamber that is filled with a fluid to a pressurized state.

6. A system according to claim 1, wherein:

said fluid of the sealed chamber of the pressurized member comprises at least one of a gas, a liquid, and a gel.

7. A system according to claim 1, further comprising:

a tube operably coupling said air pumping mechanism to said air bladder.

8. A system according to claim 1, wherein:

said air pumping mechanism comprises a pumping bulb which is manually manipulatable to inflate said air bladder to said pressurized state.

9. A system according to claim 1, further comprising:

an automatic pressure relief valve, operably coupled to said air bladder, that automatically vents said air bladder to ambient when the pressurized state of said air bladder reaches a predetermined maximum threshold pressure.

10. A system according to claim 1, further comprising:

a manual pressure relief valve, operably coupled to said air bladder, which is manually manipulated to vent said air bladder to ambient.

11. A system according to claim 1, further comprising:

a pressure gauge, in fluid communication with said air bladder, which provides a visual indication of pressure levels within said air bladder.

12. A system according to claim 1, further comprising:

a plurality of hook and loop closures, affixed to said flexible member that are joined together to securely wrap said flexible member around the leg.

13. The system according to claim 1, wherein:

said pressurized member has an oval shape.

14. A method of applying compression therapy to a saphenous vein of the human leg which extends longitudinally along the leg, the method comprising the steps of:

a) providing a device for applying pressure to the saphenous vein of the leg, said device comprising i) a flexible member having an encircling configuration that wraps around the human leg and an opened unwrapped configuration, said encircling configuration defining a central axis therethrough, said flexible member having a first length in a direction of said central axis and said flexible member having a first width when in said opened unwrapped configuration, ii) an elongate air bladder of a first size supported by said flexible member in said encircling configuration, said air bladder having a second length extending in said encircling configuration in a direction substantially parallel to the central axis and to said first length, and said elongate air bladder having a second width, said second length being at least twice said second width and said second width being less than half said first width, said air bladder capable of inflation to a pressurized state which supplies compressive forces that are directed radially inward toward the central axis and adapted due to said second length and second width to apply said compressive forces to the saphenous vein of the leg when supported by said flexible member in said encircling configuration, and iii) an air pumping mechanism, operably coupled to said air bladder, that operates to inflate said air bladder;

b) providing at least one pressurized member of a second size less than one-half said first size and having a sealed chamber filled with fluid to a pressurized state, said pressurized member separate and distinct from said flexible member and said air bladder and thus moveable relative to said flexible member and air bladder, and said pressurized member having means for adhering said pressurized member to the leg;

c) positioning said pressurized member such that it covers a treatment site and is adhered to the leg at the treatment site;

d) manipulating said flexible member such that said flexible member is securely wrapped around the leg in its encircling configuration and said air bladder chamber is secured to the leg and covers the saphenous vein of the leg, whereby the pressurized member is operably disposed between the leg and said flexible member; and e) using said air pumping mechanism to inflate said air bladder to a pressurized state that is less than 40 mmHg, wherein in the pressurized state said air bladder supplies compressive forces that are directed radially inward toward the central axis of the encircling configuration to thereby provide for application of external pressure to the saphenous vein of the leg that is covered by said air bladder, whereby said pressurized member applies increased localized pressure to the leg.

15. A method according to claim 14, wherein:

said pressurized member has peripheral portion having said means for adhering said pressurized member to the leg.

16. A method according to claim 15, wherein:

said means for adhering comprises a peel-off adhesive strip, and the positioning step c) involves peeling off the adhesive strip and affixing the pressurized member on the leg such that it covers the desired treatment site.

17. A method according to claim 14, wherein:

said pressurized member comprises two walls that define the sealed chamber that is filled with a fluid to a pressurized state.

18. A method according to claim 14, wherein:

said air pumping mechanism comprises a pumping bulb, and said inflating step e) comprises manually manipulating said pumping bulb to inflate said air bladder to said pressurized state.

19. A method according to claim 14, further comprising:

providing an automatic pressure relief valve, operably coupled to said air bladder, that automatically vents said air bladder to ambient when the internal pressure of said air bladder reaches a predetermined maximum threshold pressure.

20. A method according to claim 14, further comprising:

providing a manual pressure relief valve, operably coupled to said air bladder, which is manually manipulated to vent said air bladder to ambient.

21. A method according to claim 14, further comprising:

providing a pressure gauge, in fluid communication with said air bladder, which provides a visual indication of pressure levels within said air bladder.

22. A method according to claim 14, wherein:

said device includes a plurality of hook and loop closures, affixed to said flexible member, that are joined together to securely wrap said flexible member around the leg, and said step d) comprises manually joining said plurality of hook and loop enclosures to securely wrap said flexible member around the leg.

23. A method according to claim 14, wherein:
said air bladder applies localized pressure to the saphenous vein in order to promote healing.

24. A method according to claim 14, wherein:
the particular vein is selected from the group including the long saphenous vein and the short saphenous vein.

25. A method according to claim 14, wherein:
said pressurized member is positioned such that covers a venous ulcer and applies increased localized pressure to the venous ulcer in order to promote healing.

26. A method according to claim 14, wherein:
said pressurized member is positioned such that it covers one or more veins that are subjected to sclerotherapy.

27. A method according to claim 14, wherein:
said pressurized member is positioned such that it covers a hematoma that results from a vein harvesting procedure.

28. A kit for applying compression therapy to a saphenous vein of the human leg which extends longitudinally along the leg, the kit comprising:
   a) a flexible member having an encircling configuration that wraps around the human leg and an opened unwrapped configuration, said encircling configuration defining a central axis therethrough, said flexible member having a first length in a direction of said central axis and said flexible member having a first width when in said opened unwrapped configuration;
   b) an elongate air bladder of a first size supported by said flexible member in said encircling configuration, said air bladder having a second length extending in said encircling configuration in a direction substantially parallel to the central axis and to said first length, and said elongate air bladder having a second width, said second length being at least twice said second width and said second width being less than half said first width, said air bladder capable of inflation to a pressurized state which supplies compressive forces that are directed radially inward toward the central axis and adapted due to said second length and second width to apply said compressive forces to the saphenous vein of the leg when supported by said flexible member in said encircling configuration;
   c) an air pumping mechanism, operably coupled to said air bladder, that operates to inflate said air bladder to a pressurized state that is less than 40 mmHg, whereby in the pressurized state said air bladder provides for application of external pressure to the saphenous vein of the leg that is covered by said air bladder chamber; and
   d) a plurality of pressurized members each of a second size less than one-half said first size and each having a sealed chamber filled with fluid to a pressurized state, each separate and distinct from said flexible member and said air bladder and thus moveable relative to said flexible member and air bladder, and each having means for adhering said pressurized member to the leg, wherein at least one of pressurized members is operably disposed between the leg and the flexible member whereby it applies increased localized pressure to the leg.

29. A kit according to claim 28, wherein:
the sealed chambers of said plurality of pressurized members have varying internal pressures.

30. A kit according to claim 29, wherein:
the sealed chambers of said plurality of pressurized members have different volumes.

31. A kit according to claim 29, wherein:
the sealed chambers of said plurality of pressured members are filled with different amounts of fluid.

32. A kit according to claim 28, wherein:
said flexible member and air bladder are separate and distinct from one another and thus moveable relative to one another when the flexible member is in its unwrapped state.

33. A device according to claim 1, wherein:
said air pumping mechanism operates to inflate said air bladder to a desired pressurized state that is less than 40 mmHg, wherein the desired pressurized state can be varied.

34. A method according to claim 14, wherein:
said air pumping mechanism is operated to inflate said air bladder to a desired pressurized state that is less than 40 mmHg, wherein the desired pressurized state can be varied.

35. A kit according to claim 28, wherein:
said air pumping mechanism operates to inflate said air bladder to a desired pressurized state that is less than 40 mmHg, wherein the desired pressurized state can be varied.

* * * * *